United States Patent [19]

Goldsmith, III

[11] Patent Number: 5,053,040

[45] Date of Patent: Oct. 1, 1991

[54] METHOD OF PERFORMING A MYRINGOTOMY

[76] Inventor: Manning M. Goldsmith, III, 11 Avenue of Pines, Savannah, Ga. 31406

[21] Appl. No.: 653,154

[22] Filed: Feb. 11, 1991

Related U.S. Application Data

[62] Division of Ser. No. 434,076, Nov. 9, 1989.

[51] Int. Cl.$^5$ ............................................. A61M 27/00
[52] U.S. Cl. ..................................... 606/109; 623/10; 604/264
[58] Field of Search .................. 623/10; 606/108, 109; 128/898; 604/8, 49, 264

[56] References Cited

U.S. PATENT DOCUMENTS 3,948,271  4/1976  Akiyama ............................. 606/109
4,168,697  9/1979  Cantekin ............................. 623/66

Primary Examiner—Randy Citrin Shay
Attorney, Agent, or Firm—Rodman & Rodman

[57] ABSTRACT

An otological vent tube is supported on an apparatus that performs a myringotomy and substantially simultaneously positions the vent tube in the resulting myringotomy incision. The vent tube has proximal and distal ends and includes a central lumen that extends the full length of the tube. In all embodiments of the invention the distal end includes a distal flange in the form of a truncated cone. In some embodiments a proximal flange is provided at the proximal end, and in other embodiments the proximal flange is eliminated. The myringotomy and positioning apparatus includes an immovable outer hollow sleeve and an axially displaceable inner shaft. The distal end of the shaft is conical in form and supports the vent tube such that the distal conical end of the shaft member forms a substantial continuation of the truncated conical surface of the vent tube distal flange. The substantially continuous conical surfaces of the vent tube distal flange and the distal end of the shaft facilitates incising the tympanic membrane and insertion of the distal vent flange through the incision in a single continuous movement to install the vent tube in the membrane. The shaft is withdrawn from the vent tube while the vent tube is retained in the installed position in the tympanic membrane. The apparatus can then be removed from the outer ear passage.

7 Claims, 5 Drawing Sheets

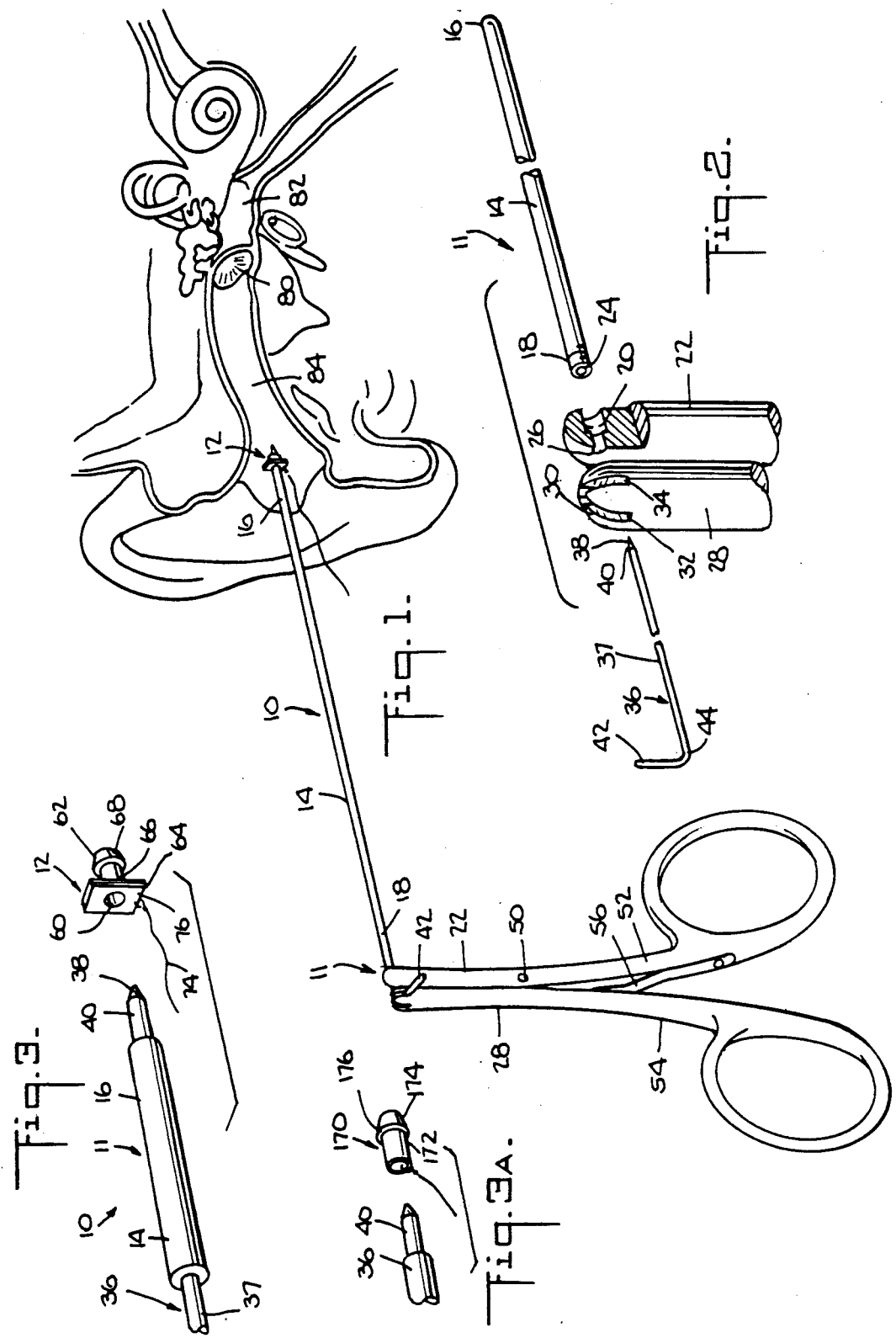

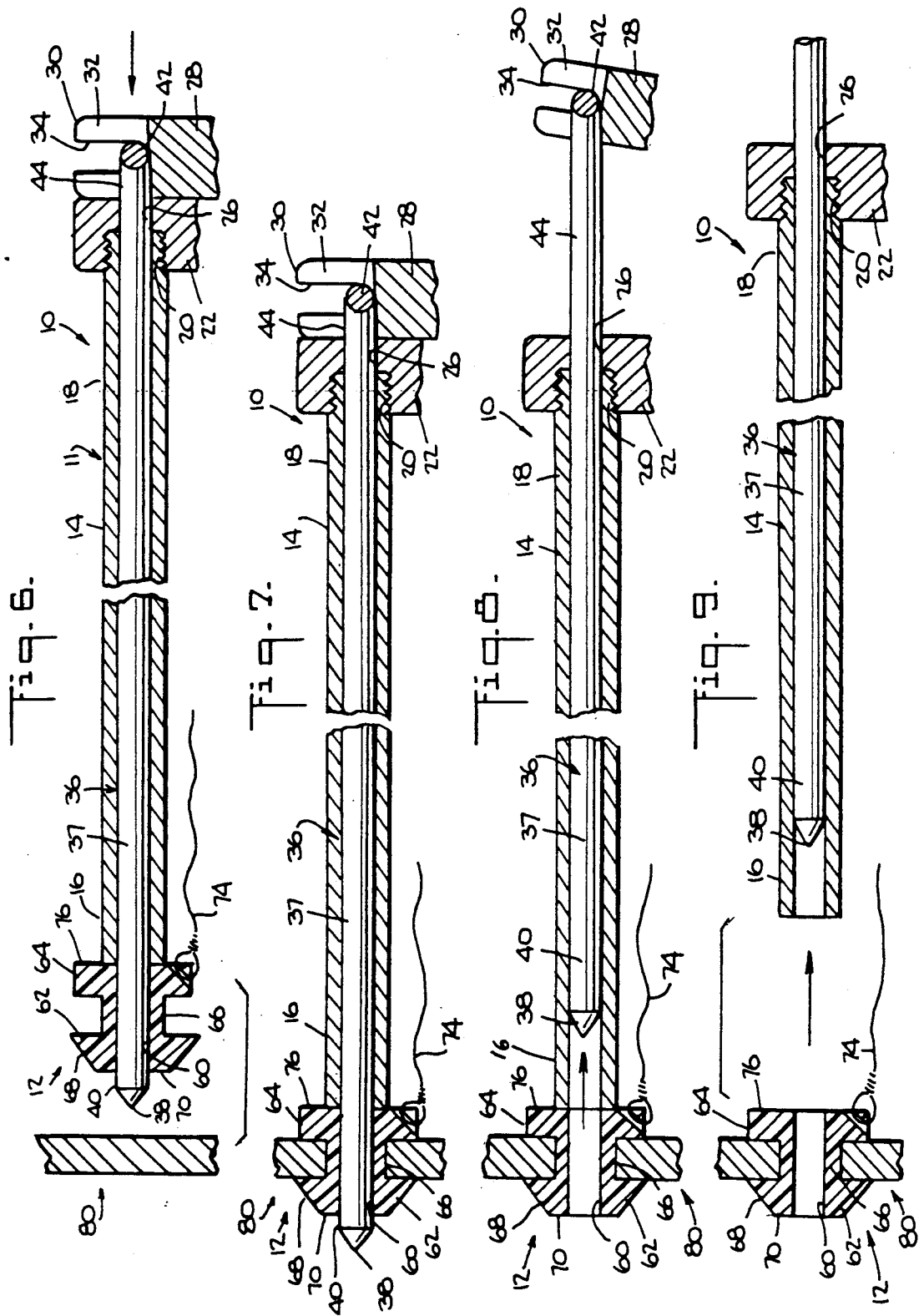

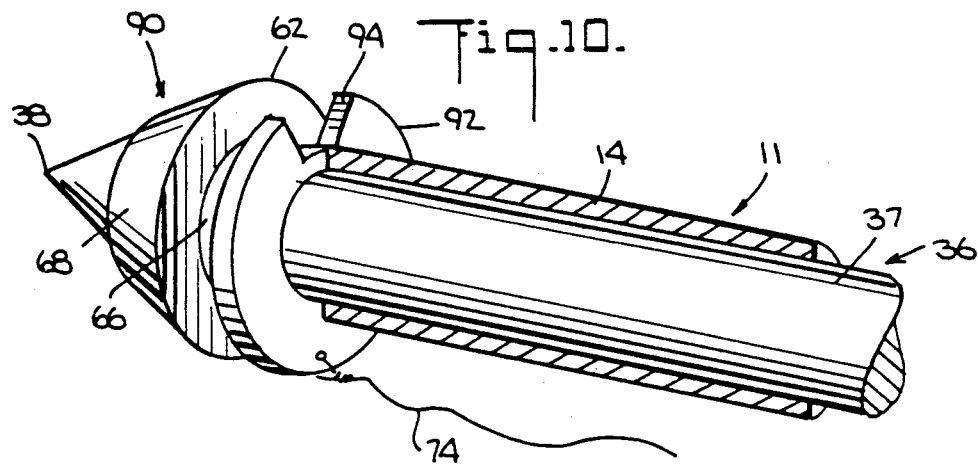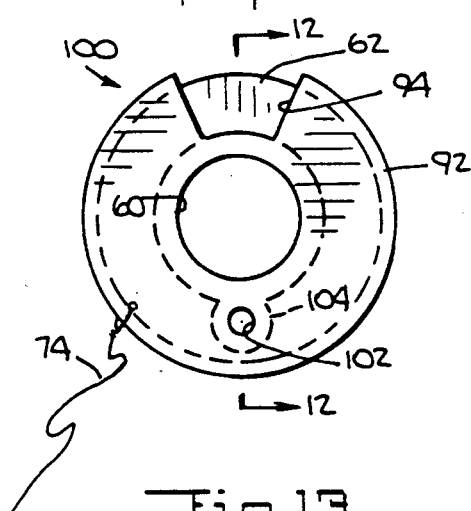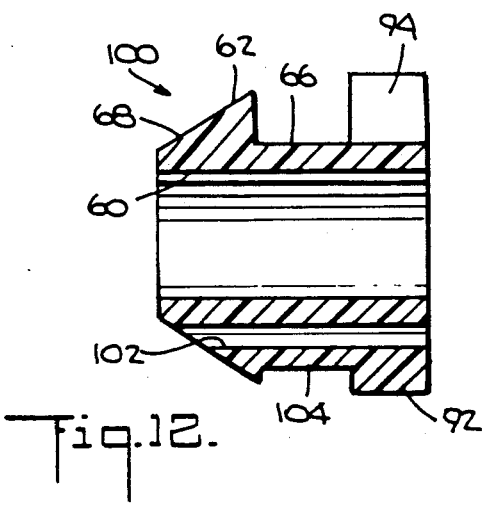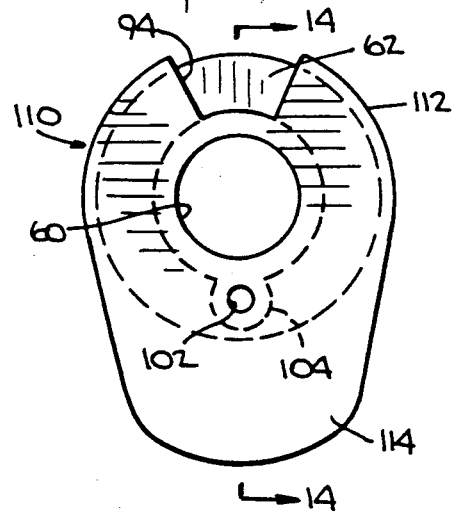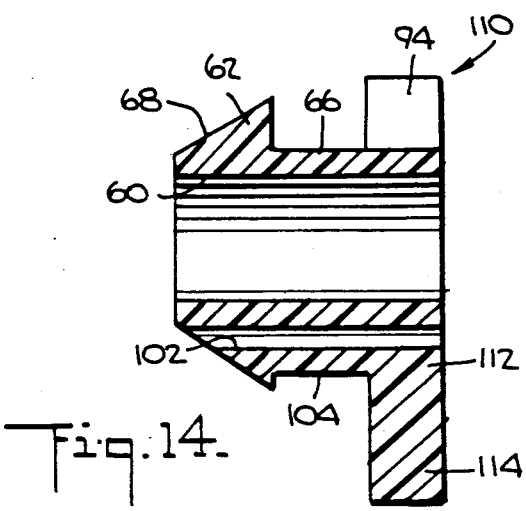

METHOD OF PERFORMING A MYRINGOTOMY

This is a division of application Ser. No. 434,076, filed Nov. 9, 1989.

BACKGROUND OF THE INVENTION

This invention relates to punch myringotomy systems and methods and more particularly to a novel otological vent tube insertion apparatus for installing a novel tube prosthesis, and a novel method of inserting a tube prosthesis in the tympanic membrane.

The installation of tubes in the tympanic membrane, which separates the middle ear passage from the outer ear passage, is a well-known remedy for treating inflammation of the middle ear or otitis media. An otitis media condition is characterized by a buildup of fluid in the middle ear passageway, causing discomfort and often adversely affecting one's hearing ability.

During treatment of otitis media, an incision is usually made through the tympanic membrane and a vent or drain in the form of a tube is inserted into the incision to permit drainage of fluid from the middle ear passage to the outer ear passage. Normally a tube is placed in each ear and generally remains in place for a predetermined time period, or until the inflammation is resolved. Removal of the tubes is usually accomplished by a relatively simple non-surgical retrieval procedure.

In many instances, otological vent tubes are formed of a resilient material such as silicone rubber or polyethylene having distal and proximal flange portions as shown in U.S. Pat. Nos. 3,645,268; 3,807,409; 3,871,380; 3,948,271; 4,168,697; and 4,650,488.

To install the tubes, a myringotomy incision is made in the tympanic membrane through which the proximal flange is inserted. In this manner the proximal and distal flange portions of the tube can be disposed on opposite sides of the tympanic membrane to maintain the tube in the incision.

Although all of the vent tubes shown in the foregoing patents permit drainage of fluid, various problems afflict many of these structures. For example, in several cases the proximal radial flanges of the known vent tubes do not have sufficient rigidity to retain the tubes in place in the tympanic membrane. The tubes thus have a tendency to slip out from their installed position. The problem of inadequate tube retention in the ear is often compounded by a forceful manner in which the vent tubes are occasionally inserted in the tympanic membranes.

The forcing of the tubes into the myringotomy incision generally causes excessive enlargement of the incision. An insecure fit of the tube in the incision can thus result, which increases the tendency of the tubes to fall from their installed position.

A further problem associated with some known vent tubes is a restricted drainage flow through the vent tube. Restricted drainage flow is often due to a provision of porous members across a central portion or passageway of the vent tube which hinders the flow of liquid material. Another source of flow restriction can be due to the configuration of the central passageway in the vent tube.

Apparatus for performing myringotomies and inserting otological vent tubes are shown, for example, in U.S. Pat. Nos. 3,530,860; 3,888,258; 3,897,786; 3,913,584; and 4,473,073.

Several of the apparatus shown in the foregoing patents include an outer sleeve and an inner axially movable shaft having a sharpened distal end portion. The sharpened distal end portion is used to puncture the tympanic membrane and can also support an otological vent tube. In many instances the otological vent tube is forced through the membrane with the shaft to puncture the membrane during insertion of the tube. However, discontinuities in the surface "envelope" of the pointed end portion of the shaft member and the puncturing portion of the otological vent tube can cause tearing and/or excessive stretching of the incision in the membrane.

As a result of such tearing and stretching of the incision, it is often difficult to obtain satisfactory positioning and retention of the otological vent tube in the tympanic membrane.

It is thus desirable to provide a punch myringotomy system which can simultaneously form an incision in the tympanic membrane and locate a tube in the incision without tearing or excessively stretching the incision during installation.

OBJECTS AND SUMMARY OF THE INVENTION

Among the several objects of the invention may be noted the provision of a novel punch myringotomy system, a novel myringotomy and otological vent tube insertion apparatus, a novel vent tube prosthesis which is simple to install and resists extrusion from the tympanic membrane once installed therein, a novel system for substantially simultaneously performing a myringotomy and installing an otological vent tube prosthesis in the resulting incision, a novel myringotomy and otological vent tube insertion apparatus which forms a substantially continuous surface envelope with a vent tube prosthesis to facilitate incision and installation of the vent tube in the incision, a novel vent tube prosthesis which includes structure for simply removing the prosthesis from an installed position, and a novel method of inserting a tube prosthesis in the tympanic membrane.

Other objects and features of the invention will be in part apparent and in part pointed out hereinafter.

The punch myringotomy system, in accordance with one embodiment of the invention, includes a resilient otological ventilation tube prosthesis and an apparatus for performing a myringotomy incision while supporting the vent tube prosthesis. The vent tube prosthesis is supported on the apparatus in a manner which enables the prosthesis to be installed substantially simultaneously with the formation of the myringotomy incision.

The vent tube prosthesis, which is formed of a resilient material, has an axially extending central lumen and axially spaced distal and proximal flanges separated by a reduced diameter portion of the vent tube. A distal end portion of the distal flange is in the form of a truncated cone having a truncated conical surface. A proximal flange at the opposite end of the tube prosthesis can be of rectangular or cylindrical form.

In one embodiment of the invention the proximal flange includes a flexible wire which can be gripped by a gripping tool to retrieve the installed tube prosthesis when such removal is desired.

In another embodiment of the invention the proximal flange is provided with an axially extending projection that can be grasped by a gripping instrument to facilitate removal of the prosthetic device from its installed position.

In a further embodiment of the invention the proximal flange of the tube prosthesis has an elongated elliptical shape to enable a portion of the proximal flange to have an exaggerated dependency from a reduced diameter portion of the tube. The exaggerated depending portion facilitates gripping by a gripping tool when removal of the installed prosthesis is desired.

In still another embodiment of the invention the proximal flange of the tube prosthesis is provided with a notched portion which functions as a viewing window to facilitate observation of the distal flange portion during installation of the tube prosthesis. Such observation is accomplished using a hand-held otoscope.

In a still further embodiment of the invention an additional drainage lumen is provided in the vent tube prosthesis below the central lumen to permit a more complete evacuation of fluid from the middle ear passage.

In another embodiment of the invention the tube prosthesis includes a distal flange in the form of a truncated cone having a conical surface, the proximal flange being eliminated. The tube, however, is of sufficient elongation to project from the tympanic membrane into the outer ear passage while extending sufficiently into the middle ear passage to ensure against dislodgment from the tympanic membrane into the middle ear passage.

The apparatus for performing the myringotomy and substantially simultaneously installing the vent tube prosthesis in the resulting incision includes a shaft for supporting the tube and for puncturing the tympanic membrane to form the incision.

A distal end portion of the shaft is in the form of a conical tip having a conical surface. The conical surface of the shaft tip is substantially continuous with the truncated conical surface at the distal flange of the vent tube prosthesis, when the vent tube prosthesis is mounted on the shaft.

The shaft is joined to one leg of a supporting device having two pivotal legs operable by scissor-like handle extensions. A sleeve member is telescoped onto the shaft and mounted to the other leg of the supporting device.

The shaft and sleeve are sized such that the distal end of the shaft projects a predetermined amount from a corresponding distal end of the sleeve. The vent tube prosthesis is sized and shaped to ensure continuity of the truncated conical surface with the shaft tip when the shaft and sleeve are assembled for installation of a vent tube.

In using the punch myringotomy system the distal end of the shaft punctures a tympanic membrane to form a myringotomy incision and the substantially continuous truncated conical surface of the distal flange penetrates the myringotomy incision substantially simultaneously after the incision is formed. The substantially continuous surfaces of the distal flange and the puncturing end of the shaft assure a smooth entry of the distal flange of the vent tube prosthesis into the incision.

Once the vent tube prosthesis has been installed in the myringotomy incision the sleeve portion of the installation apparatus is maintained in contact with a proximal flange of the tube prosthesis while the shaft portion is retracted into the sleeve. Upon sufficient retraction of the shaft into the sleeve the apparatus can be withdrawn from the outer ear passage.

In a further embodiment of the invention the distal end portion of the shaft is provided with flutes or blades that conform to the conical surface at the distal end portion of the shaft. The blades facilitate penetration of the tympanic membrane.

Since the otological vent tube prosthesis can be installed in the tympanic membrane substantially simultaneously with the formation of the myringotomy incision, any suctioning of fluid in the middle ear portion can be accomplished directly through the prosthesis rather than through the bare incision. Thus trauma to the tympanic membrane that can result when suctioning is applied through the incision is easily avoided.

The invention accordingly comprises the constructions and method hereinafter described, the scope of the invention being indicated in the claims.

DESCRIPTION OF THE DRAWINGS

In the accompanying drawings,

FIG. 1 is a simplified perspective view of a punch myringotomy system incorporating one embodiment of the invention, being inserted in an outer ear passage;

FIG. 2 is an enlarged partially exploded fragmentary detail of a shaft member, a sleeve member and a support structure thereof;

FIG. 3 is an enlarged fragmentary detail of the shaft and sleeve members and an otological vent tube prosthesis thereof;

FIG. 3a is a view similar to FIG. 3 of another embodiment of the invention;

FIG. 6 is an enlarged fragmentary sectional view of the shaft member, sleeve member and otological vent tube prosthesis thereof prior to puncturing of the tympanic membrane;

FIG. 7 is a view similar to FIG. 6 showing the membrane punctured and the vent tube positioned therein;

FIG. 8 is a view similar to FIG. 7 showing the shaft member thereof being retracted while the sleeve member maintains the vent tube in its installed position;

FIG. 9 is a view similar to FIG. 8 showing removal of the retracted shaft member and the sleeve member thereof from the site of the installed vent tube;

FIG. 10 is an enlarged fragmentary perspective view of another embodiment of the invention;

FIG. 11 is an end view of a further embodiment of the invention;

FIG. 12 is a sectional view taken on the line 12—12 of FIG. 11;

FIG. 13 is an end view of still another embodiment of the invention;

FIG. 14 is a sectional view taken on the line 14—14 of FIG. 13;

Corresponding reference characters indicate corresponding parts throughout the several views of the drawings.

DETAILED DESCRIPTION OF THE INVENTION

Figure 4:
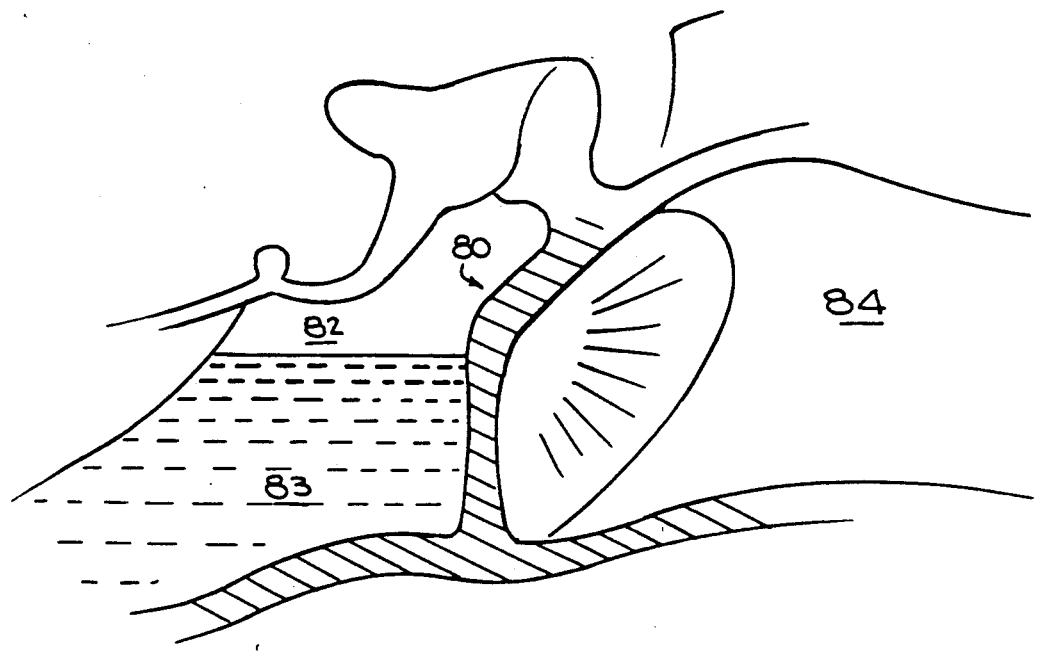
FIG. 4 is a simplified schematic sectional view of a middle and outer ear passage and tympanic membrane prior to installation of an otological vent tube prosthesis of the type shown in FIG. 3.

A punch myringotomy system incorporating one embodiment of the invention is generally indicated by the reference number 10 in FIG. 1.

The system 10 includes a myringotomy and otological vent tube insertion apparatus 11 and an otological vent tube prosthesis 12 supported at one end of the apparatus 11.

Referring to FIGS. 1-3, the apparatus 11 includes an elongated disposable sleeve member 14 having a distal end portion 16 and a proximal end portion 18. The proximal end portion 18 has a threaded outer surface that engages an internally threaded aperture 20 in a first supporting leg member 22 (FIG. 2).

The sleeve member 14 includes a central lumen 24 that aligns with an opening 26 in the supporting leg member 22 when the proximal end 18 is threaded into the aperture 20 of the leg member 22.

Referring to FIG. 1, the apparatus 11 also includes a second leg member 28 pivotally joined at 50 to the first leg member 22. The leg members 22 and 28 are provided with respective scissor-like handle extensions 52 and 54 that are normally biased away from each other by a leaf spring 56. Under this arrangement, the leg members 22 and 28 are normally biased by the leaf spring 56 into an adjacent abutting relationship as shown in FIG. 1.

The second leg member 28 has an upper end portion 30 provided with grooves 32 and 34 that criss-cross at right angles. The groove 32 aligns with the opening 26 of the first leg member 22. The aligned groove 32 and the opening 26 also align with the lumen 24 of the sleeve member 14, as most clearly shown in FIG. 2, when the sleeve member 14 is threaded into the aperture 20 of the first leg member 22.

The apparatus 11 further includes a shaft member or trocar 36 having a main body portion 37 and a pointed conical tip 38 at a distal end 40 of the main body portion 37. An arm 42 extends at right angles from a proximal end 44 of the main body portion 37.

In using the device 10, the main body portion 37 of the shaft member 36 is positioned within the central lumen 24 of the sleeve member 14. Correct positioning is accomplished by inserting the distal end portion 40 with the conical tip 38 into the groove 32 of the support leg 28. The main body portion 37 is pushed through the support leg opening 26 that aligns with the lumen 24 until the arm 42 aligns with the groove 34. The arm 42 is then rotated into the groove 34 to lock the shaft member 36 relative to the leg member 28. With the leg members 28 and 22 adjacently positioned as shown in FIGS. 1 and 2, the conical tip 38 of the main body portion 37 protrudes a predetermined amount from the distal end portion 16 of the sleeve member 14 as most clearly shown in FIG. 3.

When the handle extensions 52 and 54 of the leg members 22 and 28 are grasped and squeezed together against the bias of the spring 56, the free ends of the leg members 22 and 28 separate from one another. Separation of the leg members 22 and 28 causes the distal end portion 40 (FIG. 3) of the main body portion 37 to retract into the distal end portion 16 of the sleeve member 14.

Referring to FIGS. 3 and 6-9, the otological vent tube prosthesis 12 is preferably a resilient molding which can be formed, for example, of silicone rubber or polyethylene. The prosthesis 12 is provided with a central lumen 60 and includes an enlarged distal flange portion 62 at one end thereof and an enlarged proximal flange portion 64 at an opposite end thereof. A medial tubular portion 66 of the prosthesis 12 extends between the distal and proximal flange portions 62 and 64.

Figure 15:
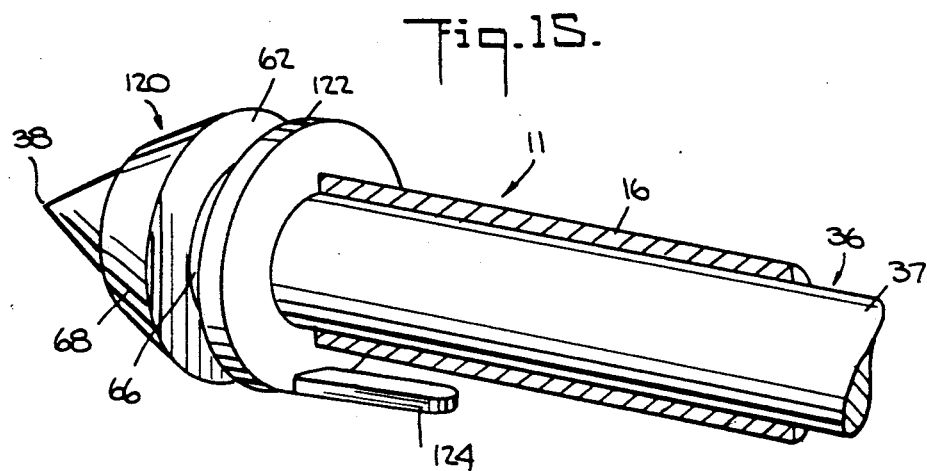
FIG. 15 is an enlarged fragmentary perspective view of a still further embodiment of the invention.

The distal flange portion 62 is in the form of a solid truncated cone having a conical surface 68 whereas the proximal flange portion 64 can be of rectangular shape as shown in FIG. 3, or of circular shape as shown in the embodiment of FIG. 15 at reference number 122. The lumen 60 extends all the way through the prosthesis from a distal end 70 to a proximal end 76.

A flexible thread-like member 74 is fastened in any suitable known manner to the proximal flange portion 64 of the prosthesis 12. The thread-like member 74 is of a predetermined length that permits gripping by a known gripping instrument (not shown) to facilitate removal of the installed prosthesis 12 when such removal is desired.

Referring to FIGS. 6 and 7, the prosthesis 12 is mounted on the distal end portion 40 of the shaft member 36 such that the proximal end surface 76 abuts against the corresponding distal end surface of the sleeve member 14. Under this arrangement, the conical surface of the conical tip 38 of the shaft member 36 forms a substantial continuation of the truncated conical surface 68 of the distal flange 62 of the prosthesis 12. It should be noted that any discontinuity shown in the drawings between the conical surface of the conical tip 38 and the truncated conical surface 68 of the prosthesis 12 in this embodiment and in subsequent embodiments is exaggerated.

The substantially continuous surfaces of the conical tip 38 and the truncated conical surface 68 of the distal flange portion 62 facilitate puncturing and distention of the tympanic membrane, shown generally at 80. Insertion of the distal flange 62 of the prosthesis 12 through the membrane 80 and into the middle ear section 82 of a patient is thus a relatively smooth procedure and does not cause excessive enlargement of the myringotomy incision.

Positioning of the prosthesis 12 in the tympanic membrane 80 and subsequent removal of the insertion apparatus 11 from a patient's outer ear passage 84 are schematically shown in FIGS. 6-9.

Referring to FIG. 6, the prosthesis 12 is supported on the distal end portion 40 of the shaft 36, in abutting relationship with the elongated sleeve member 14. The prosthesis 12 and the apparatus 11 which supports the prosthesis 12 are directed into the outer ear passage 84 (FIG. 4) and are shown just prior to puncturing and entering the tympanic membrane 80.

After the tympanic membrane 80 is punctured by the tip 38, the myringotomy incision is gradually expanded by the substantially continuous truncated conical surface 68 of distal flange 62. The incision also distends when penetrated by the truncated conical surface 68 as the distal flange 62 passes completely through the incision.

Once the distal flange 62 is past the incision, the incision becomes undistended such that the periphery of the incision which surrounds the medial portion 66 of the prosthesis 12, contracts and embraces the medial portion in a snug fitting relationship. The medial portion 66 of the prosthesis 12 is thus securely retained in the incision between the distal and proximal flanges 62 and 64 of the prosthesis 12 as shown in FIG. 7. The prosthesis 12 is thus firmly located in its installed position.

It will be noted that the support legs 22 and 28 of the apparatus 11 are not pivoted but remain adjacent during penetration of the tympanic membrane 80 by the prosthesis 12. The adjacent positioning of the supporting legs 22 and 28 maintains a predetermined protraction of the distal end 40 of the shaft member 36 that is sufficient to support the prosthesis 12 during installation. The predetermined protraction of the distal end 40 also assures the continuity of the truncated conical surface 68 with the conical tip 38.

Referring to FIG. 8, following installation of the prosthesis 12, the scissor-like handle extension 54 of the apparatus 11 is squeezed toward the handle extension 52 which is held steady. Convergence of the handle extensions 52 and 54 causes the supporting leg member 28 to move away from the supporting leg member 22. As a result, the distal end portion 40 of the shaft member 36 is drawn into the distal end portion 16 of the sleeve member 14. During such retraction of the shaft member 36, the distal end portion 16 of the sleeve member is maintained in contact with the proximal flange 64 of the prosthesis 12 to prevent inadvertent withdrawal of the prosthesis 12 from the incision in the tympanic membrane 80 while the shaft member 36 is being retracted.

Referring to FIG. 9, when the distal end portion 40 of the shaft member 36 is fully retracted into the distal end portion 16 of the sleeve member 14, the entire apparatus 11 is withdrawn from the patient's outer ear passage 84 (FIGS. 4 and 5), leaving the prosthesis 12 in place in the tympanic membrane 80, as shown schematically in FIG. 9.

Figure 5:
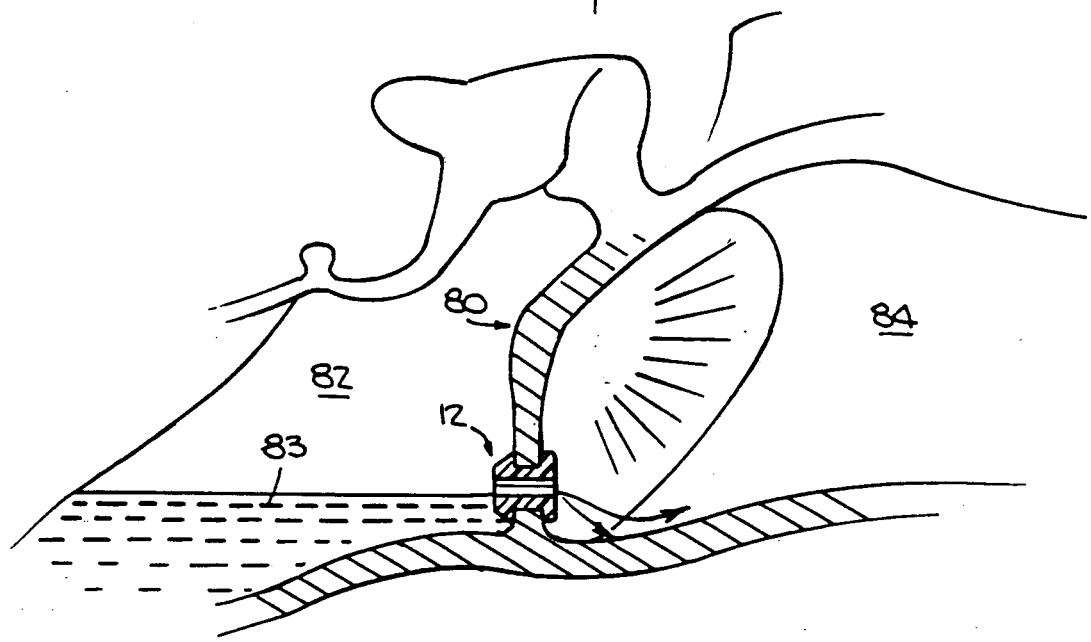
FIG. 5 is a view similar to FIG. 4 after installation of the otological vent tube prosthesis in the tympanic membrane.

Referring to FIGS. 4 and 5, an otitis media condition is schematically indicated in a middle ear passage 82 which contains a fluid 83 that has accumulated as a result of the otitis media condition. As shown schematically, the outer ear passage 84 is separated from the middle ear passage 82 by the tympanic membrane 80.

Referring to FIG. 4, prior to insertion of an otological ventilation tube prosthesis 12 into the tympanic membrane 80, the fluid 83 in the middle ear passage 84 can be a source of undesirable pressure discomfort including localized pain and reduced hearing ability.

Insertion of the prosthesis 12 in the tympanic membrane 80 establishes communication between the middle ear passage 82 and the outer ear passage 84. The accumulated fluid 83 in the middle ear passage 82 can thus drain through the prosthesis 12 into the outer ear passage 84 where it is no longer confined and easily eliminated. The drainage of fluid 83 from the middle ear passage 82 to the outer ear passage 84 relieves the pressure condition in the middle ear passage 82 and facilitates healing of the inflamed condition that is characteristic of otitis media.

Another embodiment of the otological vent tube prosthesis is generally indicated by the reference number 90 in FIG. 10. The prosthesis 90, which is mounted on the apparatus 11 in the same manner as the prosthesis 12, has some similarity with the prosthesis 12 except that a proximal flange portion 92 of the prosthesis 90 is provided with a notched portion 94. The notched portion 94 has a minor circumferential peripheral extent along the flange 92 and constitutes a viewing window for viewing the distal flange portion 62 of the prosthesis 90 during insertion of the prosthesis 90 into the tympanic membrane 80. The viewing window 94 is accessible to a known otoscope to facilitate such installation. The prosthesis 90 is otherwise identical to the prosthesis 12. Installation and operation of the prosthesis 90 is accomplished in a manner similar to that previously described for the prosthesis 12.

A further embodiment of the otological vent tube prosthesis is generally indicated by the reference number 100 in FIGS. 11 and 12. The prosthesis 100 has some similar y ·th the prosthesis 90 and further includes a second lumen 102 that is parallel to the central lumen 60. The second lumen 102 extends through a molded tubular section 104 formed on a lower part of the medial portion 66 of the prosthesis 100 as shown in FIGS. 11 and 12 and is of smaller diameter than the central lumen 60. The second lumen 102 allows the level of fluid 83 in the middle ear section 82 to be drained to a lower level than that which would be achieved by drainage only through the central lumen 60.

The extra drainage lumen 102 and the tubular section 104 are sized to cause only minimal interference with the incision that retains the prosthesis 102 in the tympanic membrane 80. The prosthesis 100 is otherwise identical to the prosthesis 90 and is mounted on the apparatus 11 for installation in the same manner as the prosthesis 12. The prosthesis 100 operates in a manner similar to that previously described for the prosthesis 12.

Still another embodiment of the otological vent tube prosthesis is generally indicated by the reference number 110 in FIGS. 13 and 14. The prosthesis 110 has some similarity with the prosthesis 100 of FIGS. 11 and 12 except that an elongated distal flange portion 112 replaces the distal flange portion 92 of the prosthesis 100. The elongated flange portion 112 has a generally truncated elliptic shape which includes a tab portion 114 at the lower portion of the flange 112.

The tab portion 114 may be grasped by a known forceps (not shown) or other known gripping instrument when it is desired to remove the prosthesis 110 from its installed position in the tympanic membrane. The flange portion 112 also includes the notch portion 94 for viewing the flange portion 62 of the prosthesis 110. The prosthesis 110 is otherwise identical to the prosthesis 100 and is mounted on an apparatus 11 in the same manner as the prosthesis 12. Installation and operation of the prosthesis 110 is accomplished in a manner similar to that previously described for the prosthesis 12.

A still further embodiment of the otological vent tube prosthesis is generally indicated by the reference number 120 in FIG. 15. The prosthesis 120, which is mounted on the apparatus 11 for installation has some similarity with the prosthesis 12 except that a proximal flange member 122 replaces the proximal flange 64 of the prosthesis 12. The proximal flange 122 of the prosthesis 120 is of generally circular configuration and includes a tab member 124 extending axially from the periphery of the flange 122 in a proximal direction.

The tab member 124 facilitates removal of the prosthesis 120 from its installed position by permitting a potentially easier grasping structure than the thread 74 of the prosthesis 12 for a known forceps or other known gripping member (not shown). The prosthesis 120 is otherwise identical to the prosthesis 12 and installation and operation of the prosthesis 120 is accomplished in a manner similar to that previously described for the prosthesis 12.

Still another embodiment of the otological vent tube prosthesis is generally indicated by the reference number 170 in FIG. 3a. The prosthesis 170 includes an elongated tube 172 having a distal flange portion 174 identical to the distal flange 62 of the prosthesis 12. The prosthesis 170 does not include a proximal flange. However the tube 172 of the prosthesis 170 extends a predetermined axial distance from a base 176 of the flange 174.

The axial extent of the tube 172 is sufficient to ensure that the distal flange 174 can project into the middle ear passage 82 without dislodgment of the prosthesis 170 into the middle ear passage 82. It has been found that a tube length of approximately 7 mm. to 12 mm. from the base 176 of the distal flange 174 is sufficient to provide the requisite projection of the distal flange 174 into the middle ear passage 82. The prescribed tube length also permits a desired length of tube 172 to extend from the tympanic membrane 80 into the outer ear passage 84. A wire 178 can be suitably attached to the proximal end of the tube 172 to facilitate retrieval of the prosthesis 170.

Installation and operation of the prosthesis 170 is accomplished in a manner similar to that previously described for the prosthesis 12. It will be noted that a distal end portion 40 of the shaft member 36 is of a length that matches the length of the tube 172 to permit the distal flange 174 to form a substantial continuation of the pointed conical tip 38 of the shaft member 36.

Figure 16:
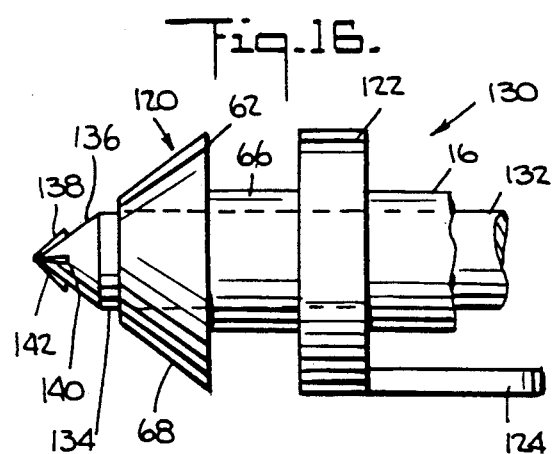
FIG. 16 is a side view of yet another embodiment of the invention.
Figure 17:
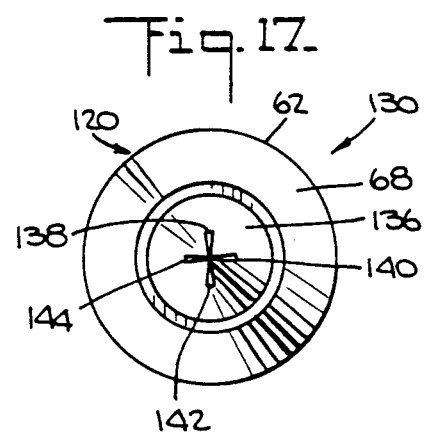
FIG. 17 is an end view thereof from the left side of FIG. 16.

Another embodiment of the otological vent tube insertion apparatus is generally indicated by the reference number 130 in FIGS. 16 and 17. The apparatus 130, has some similarity with the apparatus 11 and is shown in combination with the prosthesis 120. The apparatus 130 includes a shaft member 132 with a distal end portion 134 having a conical surface 136. A plurality of blade members 138, 140, 142 and 144 are formed to project from the conical surface 136 and extend axially from the apex of the conical surface 136 for a predetermined selected distance along the conical surface 136, such as two-thirds the length of a conical element of the surface 136. The apparatus 130 is otherwise identical to the apparatus 11 and is used to install the prosthesis 120 or any of the other previously described prostheses 12, 90, 100 and 110 in a manner similar to that previously described for the apparatus 11.

The blade members 138–142 of the apparatus 130 facilitate the initial puncturing and penetration of the tympanic membrane 80 by the conical surface 136 to form the myringotomy incision due to the cutting action of the blade members. The substantially continuous conical surfaces 136 and 68 provide for a smooth distending and stretching of the tympanic membrane 80 around the incision as previously described for the system 10. The blade members 138–142 also facilitate complete entry of the distal flange 62 of the prosthesis 120 into the middle ear passage 82. The tympanic membrane 80 at the periphery of the incision can thus securely embrace the medial portion 66 of the prosthesis 120 upon contraction of the membrane 80 after through passage of the distal flange 62.

Figure 18:
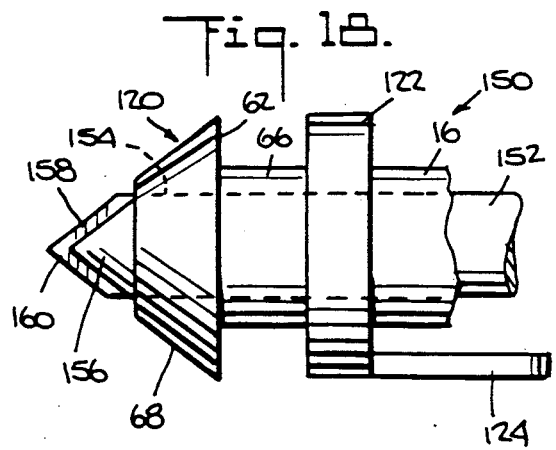
FIG. 18 is a side view of still another embodiment of the invention.
Figure 19:
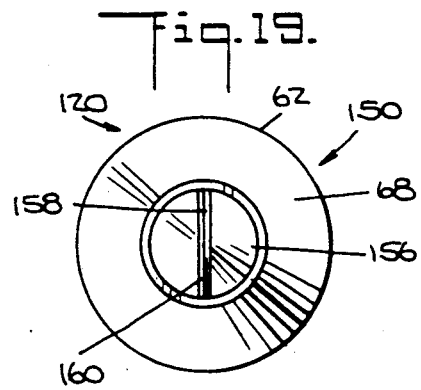
FIG. 19 is an end view thereof from the left side of FIG. 18.

A further embodiment of the otological vent tube insertion apparatus is generally indicated by the reference number 150 in FIGS. 18 and 19. The apparatus 150 has some similarity with the apparatus 130 and is shown in combination with the prosthesis 120. The apparatus 150 includes a shaft member 152 with a distal end portion 154 having a conical surface 156 that is substantially continuous with the conical surface 68 of the prosthesis 120. Two blade members 158 and 160 are formed to project from the conical surface 156 and extend axially from the apex of the conical surface 156 to the terminus of the conical surface 156. The apparatus 150 is otherwise identical to the apparatus 11 and is used to install the prosthesis 120 or any of the previously described prostheses 12, 90, 100 and 110 in a manner similar to that previously described for the prosthesis 11.

The blade members 158 and 160 facilitate initial puncturing and penetration of the tympanic membrane 80 by the conical portion 156 to form the myringotomy incision due to the cutting action of the blade members 156 and 158. As a result, there is a smooth distending and stretching of the membrane around the incision and a secure embracing of the prosthesis 120 by the incision after the prosthesis is installed.

It should be noted that the vent tube prostheses 90, 100, 110, 120, 130 and 150 can be formed with the proximal flange omitted in a manner similar to the prosthesis 170. The length of the tube from the distal flange would be in the range prescribed for the prosthesis 170.

As it will be apparent to those skilled in the art, the foregoing system and method can be employed in treating other conditions which require penetration of a membrane to permit drainage of fluid from one side to the other.

Some advantages of the invention evident from the foregoing description include an improved otological vent tube prosthesis and installation apparatus. The improved installation apparatus allows the user to substantially simultaneously perform a myringotomy and install the otological vent tube prosthesis in the resulting incision of the tympanic membrane. The apparatus is relatively simple to operate and its combination with the tube prosthesis facilitates installation of the prosthesis. The installed prosthesis helps form the myringotomy incision without excessive enlargement thereof and thus resists extrusion from the tympanic membrane.

The present invention permits a conventional two-stage procedure as previously practiced to be combined into a single operation employing a single instrument to perform both the myringotomy and the prosthesis insertion as one procedure. The installation apparatus can be used with a hand-held otoscope to facilitate performance of the myringotomy and insertion of the prosthesis.

A further advantage is that the single stage installation procedure minimizes the need for suctioning fluid from the incision during the prosthesis insertion as is often the case in known two-stage installation procedures. The present invention thus minimizes trauma to the tympanic membrane since any required suctioning can be made through the prosthesis thereby avoiding trauma to the tympanic membrane.

A still further advantage is that the prosthesis resists extrusion from the tympanic membrane during suctioning because of a substantially snug fit within the membrane This is in contradistinction with prior art systems wherein the prosthesis is inserted through a conventional myringotomy and has a tendency to extrude during suctioning because of the relatively large size of the incision compared to the size of the distal flange on the prosthesis.

Still another advantage is that there is less bleeding of the tympanic membrane following insertion of the prosthesis compared to known myringotomies. In addition, the substantially snug fit of the prosthesis within the membrane provides a more secure stable positioning of the prosthesis in the tympanic membrane than is generally obtainable with a standard myringotomy.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A method of performing a myringotomy and positioning a resilient otological vent tube having a distal end and a proximal end in the resulting myringotomy incision comprising, (a) providing an otological vent tube of predetermined length with an axially extending central lumen, and providing a distal flange in the form of a truncated cone having a truncated conical surface at a distal end portion of the tube, (b) supporting the otological vent tube on a shaft having a conical tip portion with a conical surface sized such that the truncated conical surface of the distal flange remains substantially continuous with the conical surface of the conical tip portion of the shaft during positioning of the vent tube, (c) directing the shaft and the shaft supported otological vent tube against the tympanic membrane such that the conical tip of the shaft punctures the tympanic membrane to form the myringotomy incision, and (d) penetrating the myringotomy incision substantially simultaneously with the truncated conical surface of the distal flange to distend the incision and permit smooth passage of the distal flange through the incision.

2. The method of claim 1, further providing a telescoping sleeve on the shaft to maintain the vent tube on the distal end portion of the shaft member in a predetermined position relative to the distal end portion of the shaft when the myringotomy incision is being formed by the distal end portion of the shaft, and maintaining the sleeve member in a fixed position relative to the shaft when the incision is being formed.

3. The method of claim 1, wherein the step of directing the shaft and the shaft supported otological vent tube against the tympanic membrane includes pushing the conical tip of the shaft member and the conical flange of the vent tube through the tympanic membrane in a substantially continuous movement.

4. The method of claim 1, further including retracting the conical tip portion of the shaft from the otological vent tube after the distal flange of the vent tube has been passed through the tympanic membrane while providing a predetermined restraint against an end of the vent tube opposite the distal end to ensure that the vent tube does not extrude from the incision while the shaft member is retracted.

5. The method of claim 4, including using a telescoping sleeve member that is telescoped around the shaft member to provide said predetermined restraint.

6. The method of claim 1, including choosing the selected length of the vent tube so that it is sufficient to ensure that the distal end can project into a middle ear passage without dislodgment of the tube from the passage and also permit the proximal end of the tube to extend a predetermined amount from the tympanic membrane into the outer ear passage.

7. The method of claim 1, further including providing a proximal end of the tube with a proximal flange.

* * * * *